(12) United States Patent
Lin et al.

(10) Patent No.: US 8,969,617 B2
(45) Date of Patent: Mar. 3, 2015

(54) 18β-GLYCYRRHETINIC ACID DERIVATIVES AND SYNTHETIC METHOD THEREOF

(71) Applicant: Kaohsiung Medical University, Kaohsiung City (TW)

(72) Inventors: Chun-Nan Lin, Kaohsiung (TW); Dravidum Maitraie, Kaohsiung (TW); Jih-Pyang Wang, Kaohsiung (TW); Chi-Feng Hung, Kaohsiung (TW); Huang-Yao Tu, Kaohsiung (TW); Ya-Ting Liou, Kaohsiung (TW); Bai-Luh Wei, Kaohsiung (TW); Shyh-Chyun Yang, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 49 days.

(21) Appl. No.: 13/675,574

(22) Filed: Nov. 13, 2012

(65) Prior Publication Data
US 2013/0072694 A1 Mar. 21, 2013

Related U.S. Application Data

(62) Division of application No. 12/649,437, filed on Dec. 30, 2009, now Pat. No. 8,329,940.

(30) Foreign Application Priority Data

Aug. 14, 2009 (TW) .................. 98127511 A

(51) Int. Cl.
| C07C 61/12 | (2006.01) |
| C07C 69/74 | (2006.01) |
| C07D 313/06 | (2006.01) |
| A61K 31/19 | (2006.01) |
| A61K 31/215 | (2006.01) |
| A61K 31/335 | (2006.01) |
| C07D 313/08 | (2006.01) |
| C07J 63/00 | (2006.01) |
| C07J 73/00 | (2006.01) |
| C07C 231/02 | (2006.01) |
| C07C 231/12 | (2006.01) |

(52) U.S. Cl.
CPC .............. *C07D 313/06* (2013.01); *A61K 31/19* (2013.01); *A61K 31/215* (2013.01); *A61K 31/335* (2013.01); *C07D 313/08* (2013.01); *C07J 63/008* (2013.01); *C07J 73/003* (2013.01); *C07C 231/02* (2013.01); *C07C 231/12* (2013.01)
USPC ............ 562/498; 560/116; 549/268

(58) Field of Classification Search
USPC ............ 562/498; 560/116; 549/268
See application file for complete search history.

(56) References Cited

U.S. PATENT DOCUMENTS 8,329,940 B2 12/2012 Lin et al.
2011/0039922 A1 2/2011 Lin et al.

OTHER PUBLICATIONS

Kong et al. "Inhibition of xanthine oxidase by liquiritigenin and isoliquiritigenin isolated from *Sinofranchetia chinensis*", CMLS, Cell. Mol. Life Sci., 57, 500-505 (2000).

(Continued)

*Primary Examiner* — Nizal Chandrakumar
(74) *Attorney, Agent, or Firm* — Volpe and Koenig, P.C.

(57) ABSTRACT

The present invention provides a chemical compound having the structure being one selected from a group consisting of

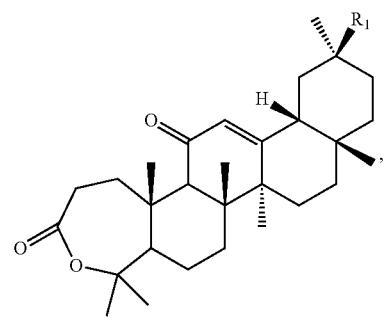

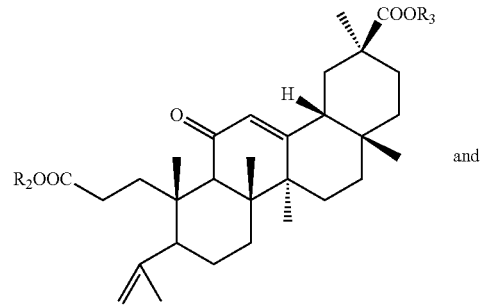

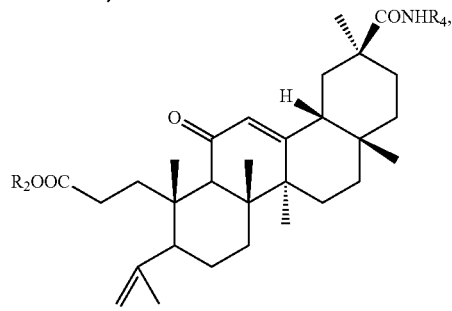

wherein $R_1$ is one selected from a group consisting of $COOCH_3$, $COOCH_2Ph$, $CONHCH(CH_3)_2$ and $CONHC_6H_5$, $R_2$ is one selected from a group consisting of H, $CH_3$ and $CH(CH_3)_2$, $R_3$ is one selected from a group consisting of H, $CH_3$, $CH(CH_3)_2$ and $CH_2Ph$, and $R_4$ is one of $CH(CH_3)_2$ and $C_6H_5$.

3 Claims, 8 Drawing Sheets

(56) References Cited

OTHER PUBLICATIONS

Maitraie, D. et al. "Synthesis, anti-inflammatory, and antioxidant activities of 18β-glycyrrhetinic acid derivatives as chemical mediators and xanthine oxidase inhibitors", Bioorganic & Medicinal Chemistry, 17, 2785-2792.

Sakano et al. STN Accession Number:1987:214165, Document Number:106:214165, "Secoglycyrrhetic acid derivatives", Abstract of JP 61148142, 4 pages.

18β-GLYCYRRHETINIC ACID DERIVATIVES AND SYNTHETIC METHOD THEREOF

This invention is a divisional application of U.S. patent application Ser. No. 12/649,437 filed Dec. 30, 2009, now published as U.S. Publication No. 2011/0039922 A1, which claims the benefit of priority to Taiwan Application No. 098127511 filed Aug. 14, 2009.

FIELD OF THE INVENTION

The present invention relates to a composition having the anti-inflammatory and the anti-oxidant activities and a synthetic method thereof. Particularly, the present invention relates to an 18β-glycyrrhetinic acid derivatives and synthetic method thereof.

BACKGROUND OF THE INVENTION

The chronic inflammatory diseases, such as rheumatoid arthritis, inflammatory bowel disease and asthma, are induced by a serial of cell inflammations in the body. The immune cells and the inflammatory cells are attracted and activated to induce inflammation at the damage or infected site when various cells (i.e. the white blood cell, the lymphocyte, the endothelial cell and epithelial cell) in the body are infected or damaged and release exceed intermediates. A cascade of the inflammations in the body is typically in association with the expressions of some inflammatory mediators, and thus it becomes a major trend to research and develop new drugs by controlling inflammation-related molecule such as nitrous oxide synthetase, reactive oxygen species (ROS).

Reactive oxygen species (ROS) is a molecule with high oxidizing ability, which is associated in mechanisms including inflammation, metabolic disorders and cellular aging. Generation of ROS may be induced by intracellular or extracellular substances. When it is overexpressed in the cells, ROS will attack DNA, protein and membrane lipid to cause the unrepairable damages, which results in cancer, aging and vascular diseases. Among the mechanisms resulting in ROS accumulation, controlling xanthine oxidase (XO) for developing the anti-XO drugs can be used to prevent or treat the diseases resulted from excess of ROS, so that it is an urgent need to develop the anti-XO drugs.

XO can transform hypoxanthine into xanthine, and then transform xanthine into uric acid. The clinical common anti-XO drug, such as allopurinol for treating gout and hyperuricemia, can cause side effect and may induce hepatitis, renal disease and allergy. Therefore, an anti-XO drug with less side effects is needed.

In view of the drawbacks of current techniques, researchers and inventors take 18β-glycyrrhetinic acid as the starting material to synthesize different derivatives of 18β-glycyrrhetinic acid by chemical reactions. After testing the biological activity, it is found that the derivatives of the present invention have inhibitory effects on inflammation and XO activity, and are valuable in developing an anti-inflammatory and anti-oxidant drug. Further, the synthesized active derivatives have a low cost and can be made in a mass production. Such chemical synthesis enables to modify the structure of the compounds for improving their activities and to estimate the yield of the compounds, which advantages the drug development. The summary of the present invention is described below.

SUMMARY OF THE INVENTION

It is an object of the present invention to provide a compound having the anti-inflammatory and the anti-oxidant activities and the synthetic method thereof. The 18β-glycyrrhetinic acid derivatives obtained by a chemical synthesis not only can be synthesized by cheaper synthetic materials, but also be made in a mass production so that they are useful in drug discovery.

According to one aspect of the present invention, a chemical compound is provided, which has a structure selected from a group consisting of

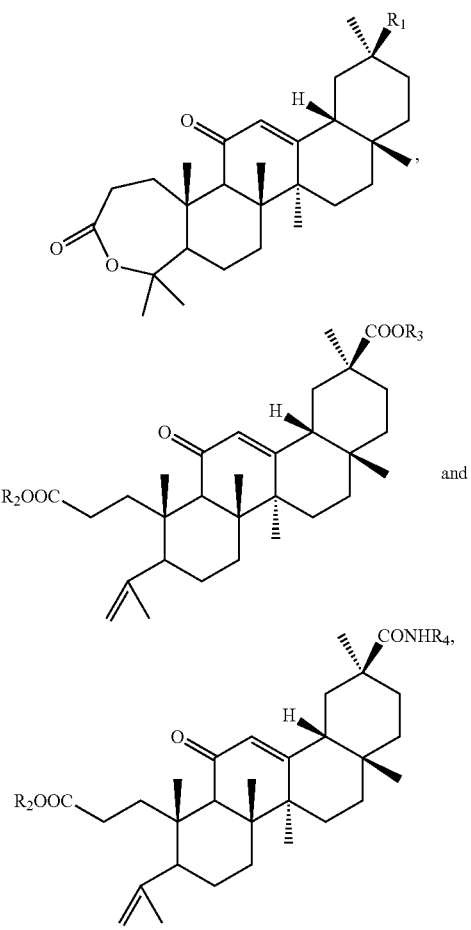

wherein $R_1$ is one selected from a group consisting of $COOCH_3$, $COOCH_2Ph$, $CONHCH(CH_3)_2$ and $CONHC_6H_5$, $R_2$ is one selected from a group consisting of H, $CH_3$ and $CH(CH_3)_2$, $R_3$ is one selected from a group consisting of H, $CH_3$, $CH(CH_3)_2$ and $CH_2Ph$, and $R_4$ is one of $CH(CH_3)_2$ and $C_6H_5$.

Preferably, the chemical compound further having at least one of an anti-inflammatory and an anti-oxidant activities.

Preferably, the chemical compound being mixed with a pharmaceutically acceptable carrier to be a pharmaceutical composition.

Preferably, the chemical compound being an active ingredient in the pharmaceutical composition.

It is another aspect of the present invention to provide a method for performing at least one function of preventing a subject from a disease and treating the disease, including the steps of providing a compound having a structure being one selected from a group consisting of

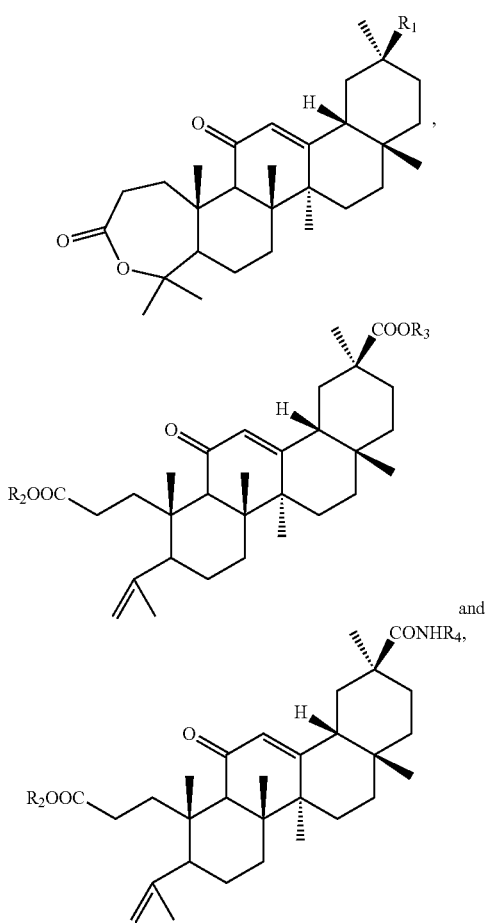

and applying the compound to the subject, wherein $R_1$ is one selected from a group consisting of $COOCH_3$, $COOCH_2Ph$, $CONHCH(CH_3)_2$ and $CONHC_6H_5$, $R_2$ is one selected from a group consisting of H, $CH_3$ and $CH(CH_3)_2$, $R_3$ is one selected from a group consisting of H, $CH_3$, $CH(CH_3)_2$ and $CH_2Ph$, and $R_4$ is one of $CH(CH_3)_2$ and $C_6H_5$.

Preferably, the disease is one of an inflammatory disease and a septic shock.

Preferably, the inflammatory disease is one of a gout and a hyperuricemia.

It is a further aspect of the present invention to provide a method for synthesizing a chemical compound, including the steps of oxidizing an 18β-glycyrrhetinic acid to form a first compound and cyclically oxidizing the first compound to obtain the chemical compound. In an exemplary embodiment, the method further includes the steps of methylating the 18β-glycyrrhetinic acid to obtain a methylated 18β-glycyrrhetinic acid and oxidizing the methylated 18β-glycyrrhetinic acid to obtain the first compound.

According to the present invention, the method further includes a step of esterifying the chemical compound to obtain a first derivative of the chemical compound.

According to the present invention, the method further includes a step of cleaving a lactone ring from the chemical compound to obtain a second derivative of the chemical compound.

According to the present invention, the method further includes a step of treating second derivative with an alcohol solution to obtain a third derivative of the chemical compound.

Preferably, the alcohol solution is one of an isopropyl alcohol solution and a benzyl alcohol solution.

According to the present invention, the method further includes a step of treating the second derivative with an amine solution to obtain a fourth derivative of the chemical compound.

Preferably, the amine solution is one of an isopropylamine solution and an aniline solution.

According to the present invention, the method further includes the steps of treating the chemical compound with an alcohol solution and cleaving a lactone ring of the chemical compound treated by the alcohol solution to obtain a fifth derivative of the chemical compound.

According to the present invention, the method further includes the steps of treating the chemical compound with an amine solution and cleaving a lactone ring of the chemical compound treated by the amine solution to obtain a sixth derivative of the chemical compound.

Preferably, the first compound is transformed into the chemical compound.

Other objects, advantages and efficacies of the present invention will be described in detail below taken from the preferred embodiments with reference to the accompanying drawings, in which:

DETAILED DESCRIPTION OF THE PREFERRED EMBODIMENT

The present invention will now be described more specifically with reference to the following embodiments. It is to be noted that the following descriptions of preferred embodiments of this invention are presented herein for the purposes of illustration and description only; it is not intended to be exhaustive or to be limited to the precise form disclosed.

The present invention provides a compound having the anti-inflammatory and the anti-oxidant activities, which is an 18β-glycyrrhetinic acid derivative, and the synthetic method thereof is described as follows.

Example I

Preparation of the Compound 6

Figure 1:
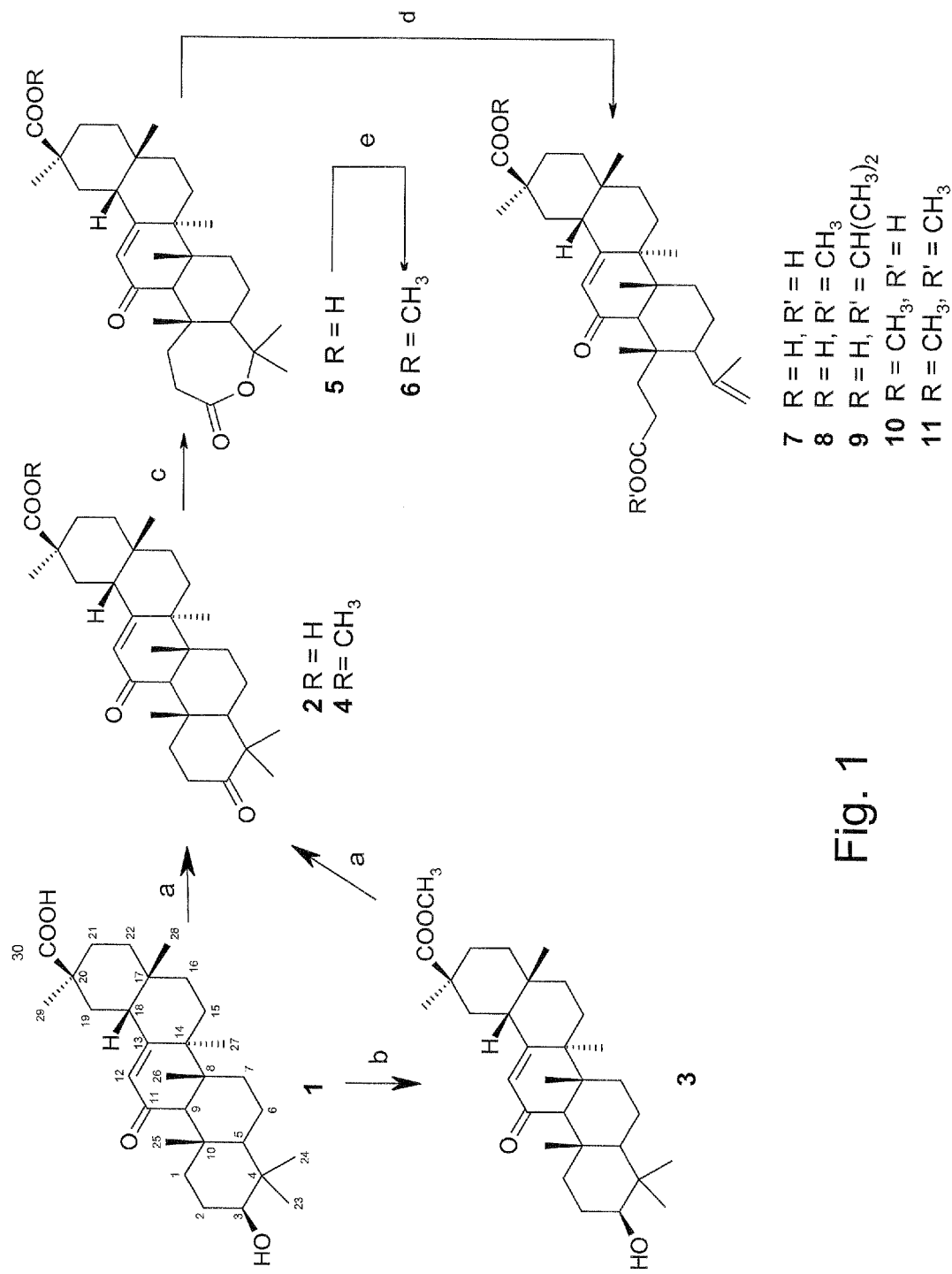
FIG. 1 is a flow chart illustrating the processes in the present invention for synthesizing the 18β-glycyrrhetinic acid derivatives 2-11, wherein each number represents a different compound.

Please refer to FIG. 1, which is the first flow chart in the present invention for synthesizing the 18β-glycyrrhetinic acid derivatives, wherein each number represents a different compound. Starting material, 18β-GA (compound 1) was oxidized to 3-keto compound 2 using $CrO_3$ in dimethyl formamide (DMF) for 12 hrs (step a). Compound 2 is dissolved in $CH_2Cl_2$ and m-chloroperbenzoic acid (m-CPBA) is added therein as an oxidizing agent at room temperature for 12 hrs to afford a lactone compound 5 (step c, a cyclic oxidation). Alternatively, if a methylated 18β-GA (compound 3) is obtained by methylating the starting material 18β-GA (step b) and then $CrO_3$ is added into the compound 3 in DMF at room temperature for 12 hrs oxidization, a compound 4 is afforded (with the same with step a). Compound 4 is further treated with m-CPBA in DMF at room temperature for 12 hrs to give 3,4 lactone 30 methyl ester (compound 6). The compound 6 is synthesized in a different synthetic route, by the esterification of lactone compound 5 using 1-ethyl-3-(3-dimethylaminopropyl)carbodiimide (EDCI) as an activating agent in methanol containing $CH_2Cl_2$ and 4-dimethylaminopyridine (DMAP) (step e).

Compound 4 (1 g, 2.1 mmol) is dissolved in $CH_2Cl_2$ (30 mL) and 3-chloroperoxybenzoic acid (3.6 g, 21.3 mmol) is added therein. The mixture is allowed to stay at room temperature in dark for 12 hrs. The solution is diluted with $CHCl_3$, washed with 5% KI solution and 5% sodium sulfite solution, dried over $Na_2SO_4$, and concentrated, so as to give 3,4 lactone 30 methyl ester (compound 6), as a white solid (0.82 g, 1.6 mmol, 78%): mp 166-171° C.; $[\alpha]_D^{25}$ 189 (c 0.1, $CHCl_3$). IR (KBr): 1715, 1648 cm$^{-1}$. $^1$H NMR (CDCl$_3$): δ 0.67 (3H, s, Me-28), 1.10 (3H, s, Me-29), 1.11 (3H, s, Me-26), 1.33 (6H, s, Me-25 and Me-27), 1.40 (3H, s, Me-23), 1.43 (3H, s, Me-24), 3.64 (3H, s, —OCH$_3$), 5.65 (1H, s, H-12). $^{13}$C NMR (CDCl$_3$): see Table 1. EIMS (70 eV) m/z (% rel. int.): 498 [M]$^+$ (3). HRESIMS: Calcd for $C_{31}H_{46}O_5Na$: 521.3243. Found: 521.3241.

Example II

Preparation of Compounds 7-11

The lactone ring of the compounds 5 or 6 is cleaved by treatment of adding P-toluenesulfonic acid (p-TSA) in an appropriate solvent, such as isopropyl alcohol and dichloromethane, to yield compounds 7-11 (step d). Compound 5 (0.1 g, 0.2 mmol) is dissolved in isopropyl alcohol (5 mL) and $CH_2Cl_2$ (2 mL), and 0.3 g of p-toluenesulfonic acid is added thereinto. The mixture is stirred at room temperature for 6-8 h, concentrated in vacuo, poured into water, extracted with $CHCl_3$. The $CHCl_3$ layer is washed with 5% sodium bicarbonate and brine, dried over $Na_2SO_4$, and concentrated. The residue is purified by a column to yield compound 9, as a light yellow solid (0.06 g, 0.12 mmol, 60%): mp 94-99° C.; $[\alpha]_D^{25}$ 154 (c 0.1, $CHCl_3$). IR (KBr): 2976, 1727, 1658, 1459, 1382, 1175 cm$^{-1}$. $^1$H NMR (CDCl$_3$): δ 0.85 (3H, s, Me-28), 1.16 (3H, s, Me-29), 1.17 (3H, s, Me-25), 1.19 (3H, s, Me-26), 1.21 (6H, d, J=6.4 Hz, CH(CH$_3$)$_2$), 1.39 (3H, s, Me-27), 1.76 (3H, s, Me-24), 4.69 (1H, br s, H-23), 4.89 (1H, br s, H-23), 4.95 (1H, m, —OCH), 5.72 (1H, s, H-12). $^{13}$C NMR (CDCl$_3$): see Table 1. EIMS (70 eV) m/z (% rel. int.): 526 [M]$^+$ (2). HRESIMS: Calcd for $C_{33}H_{50}O_5Na$: 549.3556. Found: 549.3554.

Dissolving Compound 6 (0.1 g, 0.2 mmol) in $CH_2Cl_2$ (10 mL) and adding 0.3 g p-toluenesulfonic acid thereinto. The mixture is stirred at room temperature for 6-8 h. The mixture is diluted with water and extracted with $CHCl_3$. The organic layer is washed with 5% sodium bicarbonate solution, dried over MgSO4, filtered, and concentrated. The residue is purified by a column to give compound 10 as a white solid (0.08 g, 0.16 mmol, 78%): mp 89-94° C.; $[\alpha]_D^{25}$ 171 (c 0.1, $CHCl_3$). IR (KBr): 1729, 1658 cm$^{-1}$. $^1$H NMR (CDCl$_3$): δ 0.78 (3H, s, Me-28), 1.12 (3H, s, Me-29), 1.13 (6H, s, Me-25 and Me-26), 1.35 (3H, s, Me-27), 1.72 (3H, s, Me-24), 3.66 (3H, s, —COOCH$_3$), 4.66 (1H, br s, H-23), 4.86 (1H, br s, H-23), 5.65 (1H, s, H-12). $^{13}$C NMR (CDCl$_3$): see Table 1. EIMS (70 eV) m/z (% rel. int.): 498 [M]$^+$ (10). HRESIMS: Calcd for $C_{31}H_{46}O_5Na$: 521.3243. Found: 521.3245.

Example III

Preparation of Compounds 12-15

General procedure for esterification and amidation of lactone (such as compounds 5 and 6) and seco-compounds (such as compounds 7-11) obtained by the processes above are described as follows. To a solution of lactone or seco-compound (1 mmol) in $CH_2Cl_2$ (10 mL) are added EDCI (2 mmol) and a catalytic amount of DMAP followed by an alcohol or an amine solution (2 mmol) in accordance with various compounds. The reacted mixture is stirred at room temperature overnight. After the reaction is finished (monitored by TLC), the mixture is diluted with water and extracted with chloroform. The organic solution is washed with 3% hydrochloric acid solution, brine, dried over MgSO$_4$, and filtered. The solvent is removed in vacuo and the product is purified by column chromatography.

Figure 2:
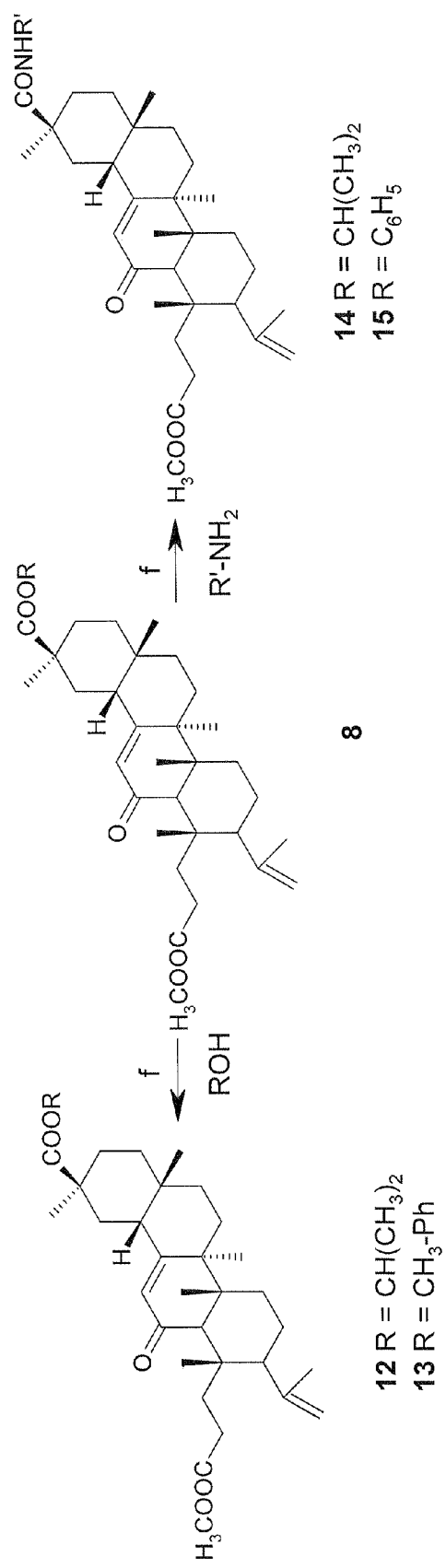
FIG. 2 is a flow chart illustrating the processes in the present invention for synthesizing the 18β-glycyrrhetinic acid derivatives 12-15, wherein each number represents a different compound.

Please refer to FIG. 2, which is the second flow chart in the present invention for synthesizing the 18β-glycyrrhetinic acid derivatives. According to the general procedures and the reacting amount for preparing the compound 12-15, seco-methyl ester 8 is treated with isopropyl alcohol and benzyl alcohol in the presence of EDCI and 4-dimethylaminopyridine (DMAP) to provide the corresponding 30-ester compounds 12 and 13, respectively (step f). Using the similar procedures, seco-methyl ester 8 is treated with isopropylamine and aniline to afford a 30-amide seco-compounds 14 and 15, respectively.

Compound 12 is obtained as light yellow solid (0.28 g, 0.52 mmol, 52%): mp 116-119° C.; $[\alpha]_D^{25}$ 126 (c 0.1, $CHCl_3$). IR (KBr): 1724, 1658 cm$^{-1}$. $^1$H NMR (CDCl$_3$): δ 0.79 (3H, s, Me-28), 1.11 (3H, s, Me-29), 1.14 (3H, s, Me-25), 1.15 (3H, s, Me-26), 1.21 (3H, d, J=6.4 Hz, —CHCH$_3$), 1.24 (3H, d, J=6.4 Hz, —CHCH$_3$), 1.37 (3H, s, Me-27), 1.74 (3H, s, Me-24), 3.60 (3H, s, OCH$_3$), 4.67 (1H, br s, H-23), 4.87 (1H, br s, H-23), 5.02 (1H, septet, J=6.4 Hz, OCH), 5.63 (1H, s, H-12). $^{13}$C NMR (CDCl$_3$): see Table 1. EIMS (70 eV) m/z (% rel. int.): 540 [M]$^+$ (18). HRESIMS: Calcd for C$_{34}$H$_{52}$O$_5$Na: 563.3712. Found: 563.3711.

Compound 13 is obtained as light yellow solid (0.35 g, 0.6 mmol, 60%): mp 32-38° C.; [α]$_D$$^{25}$ 120 (c 0.1, CHCl$_3$). IR (KBr): 1730, 1657 cm$^{-1}$. $^1$H NMR (CDCl$_3$): δ 0.72 (3H, s, Me-28), 1.12 (3H, s, Me-29), 1.14 (3H, s, Me-25), 1.15 (3H, s, Me-26), 1.35 (3H, s, Me-27), 1.74 (3H, s, Me-24), 3.59 (3H, s, —OCH$_3$), 4.67 (1H, br s, H-23), 4.87 (1H, br s, H-23), 5.07 (1H, d, J=12 Hz, —CHH—C$_6$H$_5$), 5.19 (1H, d, J=12 Hz, CHH—C$_6$H$_5$), 5.55 (1H, s, H-12), 7.35 (5H, m, C$_6$H$_5$). $^{13}$C NMR (CDCl$_3$): see Table 1. EIMS (70 eV) m/z (% rel. int.): 588 [M]$^+$ (3). HRESIMS: Calcd for C$_{38}$H$_{52}$O$_5$Na: 611.3712. Found: 611.3709.

Compound 14 is obtained as light yellow solid (0.34 g, 0.63 mmol, 63%): mp 80-85° C.; [α]$_D$$^{25}$ 116 (c 0.1, CHCl$_3$). IR (KBr): 3379, 1720, 1645 cm$^{-1}$. $^1$H NMR (CDCl$_3$): δ 0.82 (3H, s, Me-28), 1.11 (3H, s, Me-29), 1.13, 1.15 (6H, each d, J=6.4 Hz, —CH(CH$_3$)$_2$), 1.15 (3H, s, Me-26), 1.16 (3H, s, Me-25), 1.39 (3H, s, Me-27), 1.75 (3H, s, Me-24), 3.62 (3H, s, OCH$_3$), 4.11 (1H, m, NCH), 4.68 (1H, br s, H-23), 4.89 (1H, br s, H-23), 5.37 (1H, d, J=8.4, —NH), 5.64 (1H, s, H-12). $^{13}$C NMR (CDCl$_3$): see Table 1. EIMS (70 eV) m/z (% rel. int.): 539 [M]$^+$ (34). HRESIMS: Calcd for C$_{34}$H$_{53}$NO$_4$Na: 562.3872. Found: 562.3874.

Compound 15 is obtained as light yellow solid (0.38 g, 0.66 mmol, 66%): mp 149-154° C.; [α]$_D$$^{25}$ 192 (c 0.1, CHCl$_3$). IR (KBr): 3375, 1728, 1655, 1598 cm$^{-1}$. $^1$H NMR (CDCl$_3$): δ 0.83 (3H, s, Me-28), 1.15 (3H, s, Me-25), 1.16 (3H, s, Me-26), 1.26 (3H, s, Me-29), 1.41 (3H, s, Me-27), 1.75 (3H, s, Me-24), 3.63 (3H, s, OCH3), 4.69 (1H, br s, H-23), 4.89 (1H, br s, H-23), 5.72 (1H, s, H-12), 7.11 (1H, brt, J=8.4 Hz, aromatic H), 7.33 (2H, br t, J=8.4 Hz, aromatic H), 7.37 (1H, br s, NH), 7.51 (1H, dd, J=8.4 Hz, 1.2 Hz, aromatic H). $^{13}$C NMR (CDCl$_3$): see Table 1. EIMS (70 eV) m/z (% rel. int.): 573 [M]$^+$ (32). HRESIMS: Calcd for C$_{37}$H$_{51}$NO$_4$Na: 596.3716. Found: 596.3718.

Example IV

Preparation of Compounds 16-21

Figure 3:
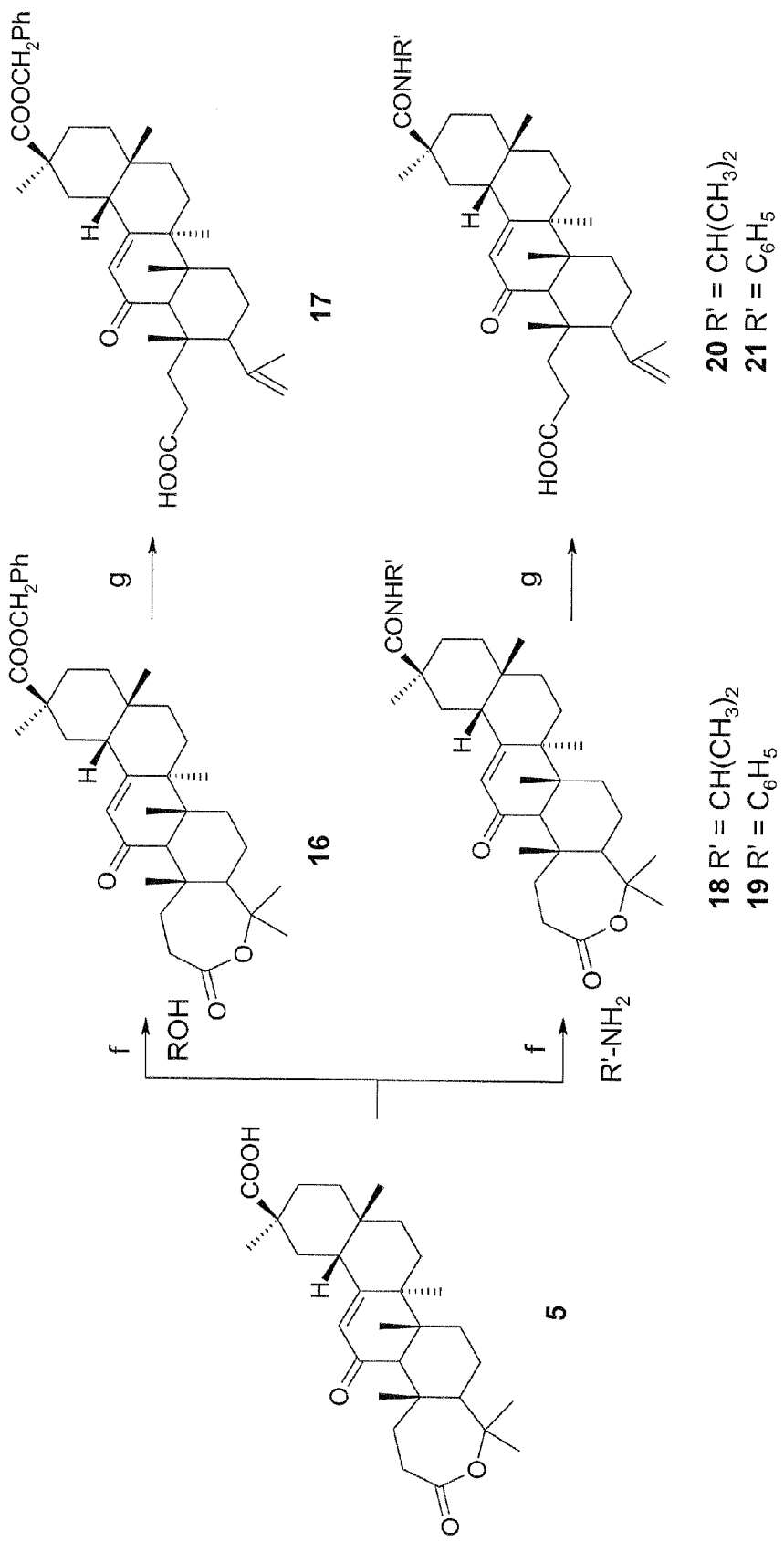
FIG. 3 is a flow chart illustrating the processes in the present invention for synthesizing the 18β-glycyrrhetinic acid derivatives 16-21, wherein each number represents a different compound.

Please refer to FIG. 3, which is the third flow chart in the present invention for synthesizing the 18β-glycyrrhetinic acid derivatives. Similar to the general procedures and reacting amount in the second flow chart, compounds 16, 18, and 19 are prepared from lactone compound 5 in CH$_2$Cl$_2$ in the presence of EDCI and DMAP for 24 hrs (the same as the step f). As shown in FIG. 3, acid group at C-30 of compound 5 is modified to ester (compound 16) and amide (compounds 18 and 19) respectively during the synthesis of compounds 16, 18 and 19. Then, the ring of the compounds 16, 18 and 19 are cleaved in the presence of p-TSA in methylene chloride for 24 hrs and the C-30 substituted seco-acids compounds 17, 20, and 21 are yielded (step g).

Compound 16 is synthesized by esterifying compound 5 using benzyl alcohol following the general procedure described above. Compound 16 is obtained as a white solid (0.36 g, 0.62 mmol, 62%): mp 83-89° C.; [α]$_D$$^{25}$ 254 (c 0.1, CHCl$_3$). IR (KBr): 1726, 1654 cm$^{-1}$. $^1$H NMR (CDCl$_3$): δ 0.73 (3H, s, Me-28), 1.14 (3H, s, Me-29), 1.16 (3H, s, Me-26), 1.36 (3H, s, Me-25), 1.37 (3H, s, Me-27), 1.44 (3H, s, Me-23), 1.47 (3H, s, Me-24), 5.08 (1H, d, J=12.4 Hz, —OCHH—), 5.21 (1H, d, J=12.4 Hz, —OCHH—), 5.58 (1H, s, H-12), 7.36 (5H, m, aromatic proton). $^{13}$C NMR (CDCl$_3$): see Table 1. EIMS (70 eV) m/z (% rel. int.): [M]$^+$ 574 (15). HRESIMS: Calcd for C$_{37}$H$_{50}$O$_5$Na: 597.3556. Found: 597.3553.

Compound 17 is prepared by cleaving the lactone ring of the compound 16 following the procedure described above. Compound 17 is obtained as a white solid (0.08 g, 0.14 mmol, 70%): mp 87-92° C.; [α]$_D$$^{25}$ 145 (c 0.1, CHCl$_3$). IR (KBr): 1726, 1657 cm$^{-1}$. $^1$H NMR (CDCl$_3$): δ 0.73 (3H, s, Me-28), 1.15 (3H, s, Me-29), 1.16 (6H, s, Me-25 and 26), 1.36 (3H, s, Me-27), 1.75 (3H, s, Me-24), 4.69 (1H, br s, H-23), 4.89 (1H, br s, H-23), 5.09 (1H, d, J=12.4 Hz, —OCHH—), 5.21 (1H, d, J=12.4 Hz, —OCHH—), 5.57 (1H, s, H-12), 7.37 (5H, m, C6H5). $^{13}$C NMR (CDCl$_3$): see Table 1. EIMS (70 eV) m/z (% rel. int.): [M]$^+$ 574 (25). HRESIMS: Calcd for C$_{37}$H$_{50}$O$_5$Na: 597.3556. Found: 597.3558.

Compound 18 is synthesized by amidating the compound 5 using iso-propylamine following the general procedure described above. Compound 18 is obtained as a light yellow solid (0.32 g, 0.6 mmol, 60%): mp 94-99° C.; [α]$_D$$^{25}$ 154 (c 0.1, CHCl$_3$). IR (KBr): 3382, 1720, 1653 cm$^{-1}$. $^1$H NMR (CDCl$_3$): δ 0.77 (3H, s, Me-28), 1.07 (3H, s, Me-29), 1.11 (3H, s, Me-26), 1.33 (3H, s, Me-27), 1.34 (3H, s, Me-25), 1.40 (3H, s, Me-23), 1.44 (3H, s, Me-24), 4.07 (1H, m, CH(CH$_3$)$_2$), 5.52 (1H, d, J=8.0 Hz, NH), 5.64 (1H, s, H-12). $^{13}$C NMR (CDCl$_3$): see Table 1. EIMS (70 eV) m/z (% rel. int.): 525 [M]$^+$ (27). HRESIMS: Calcd for C$_{33}$H$_{51}$NO$_4$Na: 548.3716. Found: 548.3717.

Compound 19 is synthesized by amidating the compound 5 using aniline following the general procedure described above. Compound 19 is obtained as a white solid (0.37 g, 0.66 mmol, 66%): mp 123-128° C.; [α]$_D$$^{25}$ 268 (c 0.1, CHCl$_3$). IR (KBr): 3359, 1717, 1655 cm$^{-1}$. $^1$H NMR (CDCl$_3$): δ 0.81 (3H, s, Me-28), 1.16 (3H, s, Me-29), 1.26 (3H, s, Me-26), 1.37 (3H, s, Me-27), 1.41 (3H, s, Me-25), 1.44 (3H, s, Me-23), 1.48 (3H, s, Me-24), 5.75 (1H, s, H-12), 7.11 (1H, m, aromatic proton), 7.34 (3H, m, NH, and aromatic proton), 7.50 (2H, m, aromatic proton). $^{13}$C NMR (CDCl$_3$): see Table 1. EIMS (70 eV) m/z (% rel. int.): 559 [M]$^+$ (20). HRESIMS: Calcd for C$_{36}$H$_{49}$NO$_4$Na: 582.3559. Found: 582.3557.

Compound 20 is prepared by cleaving the lactone ring of the compound 18 following the procedure described above. Compound 20 is obtained as a light yellow solid (0.06 g, 0.12 mmol, 62%): mp 142-146° C.; [α]$_D$$^{25}$ 126 (c 0.1, CHCl$_3$). IR (KBr): 3348, 1738, 1651 cm$^{-1}$. $^1$H NMR (CDCl$_3$): δ 0.81 (3H, s, Me-28), 1.11 (6H, d, J=6.8 Hz, —CH(CH$_3$)$_2$), 1.12 (3H, s, Me-29), 1.15 (6H, s, Me-25, and Me-26), 1.37 (3H, s, Me-27), 1.74 (3H, s, Me-24), 4.11 (1H, m, —CH(CH$_3$)$_2$), 4.68 (1H, br s, H-23), 4.88 (1H, br s, H-23), 5.64 (1H, s, H-12), 5.71 (1H, d, J=8.0 Hz, NH). $^{13}$C NMR (CDCl$_3$): see Table 1. EIMS (70 eV) m/z (% rel. int.): 525 [M]$^+$ (32). HRESIMS: Calcd for C$_{33}$H$_{51}$NO$_4$Na: 548.3716. Found: 548.3718.

Compound 21 is prepared by cleaving the lactone ring of the compound 19 following the procedure described above. Compound 21 is obtained as a white solid (0.07 g, 0.13 mmol, 65%): mp 162-166° C.; [α]$_D$$^{25}$ 262 (c 0.1, CHCl$_3$). IR (KBr): 3365, 1652, 1526 cm$^{-1}$. $^1$H NMR (CDCl$_3$): δ 0.84 (3H, s, Me-28), 0.97 (3H, s, Me-25), 1.00 (3H, s, Me-26), 1.31 (3H, s, Me-29), 1.40 (3H, s, Me-27), 1.69 (3H, s, Me-24), 4.62 (1H, br s, H-23), 4.86 (1H, br s, H-23), 5.84 (1H, s, H-12), 7.07 (1H, m, aromatic proton), 7.28 (2H, m, aromatic proton), 7.45 (2H, m, aromatic proton), 8.27 (1H, br s, NH). $^{13}$C NMR (CDCl$_3$): see Table 1. EIMS (70 eV) m/z (% rel. int.): 559 [M]$^+$ (64). HRESIMS: Calcd for C$_{36}$H$_{49}$NO$_4$Na: 582.3559. Found: 582.3558.

TABLE 1

13C NMR Spectral Data for Compounds 6, 9, 10, and 12-21.

| Position | 6 | 9 | 10 | 12 | 13 | 14 | 15 | 16 | 17 | 18 | 19 | 20 | 21 |
|---|---|---|---|---|---|---|---|---|---|---|---|---|---|
| C-1 | 38.7 | 23.5 | 23.7 | 23.7 | 23.7 | 23.7 | 23.8 | 38.6 | 23.8 | 38.7 | 38.6 | 23.7 | 23.5 |
| C-2 | 32.1 | 31.8 | 31.0 | 31.4 | 31.3 | 31.4 | 31.4 | 32.0 | 31.4 | 32.1 | 32.0 | 31.4 | 31.4 |
| C-3 | 175.4 | 173.5 | 179.6 | 175.7 | 176.1 | 174.6* | 173.9* | 176.1 | 179.0 | 175.5 | 175.6 | 179.0 | 180.6 |
| C-4 | 85.5 | 146.6 | 146.4 | 146.5 | 146.4 | 146.5 | 146.5 | 85.6 | 146.5 | 85.6 | 85.6 | 146.4 | 146.3 |
| C-5 | 54.2 | 38.7 | 38.6 | 38.7 | 38.6 | 38.7 | 38.8 | 54.5 | 38.7 | 54.2 | 54.5 | 38.7 | 39.1 |
| C-6 | 22.0 | 29.7 | 29.0 | 28.6 | 28.4 | 28.6 | 28.4 | 22.0 | 28.4 | 22.0 | 22.0 | 28.6 | 28.8 |
| C-7 | 32.0 | 34.3 | 34.1 | 34.4 | 34.3 | 34.4 | 34.4 | 32.4 | 34.2 | 32.2 | 32.4 | 34.1 | 34.1 |
| C-8 | 43.3 | 43.6 | 40.3 | 43.6 | 43.9 | 43.3 | 43.7 | 43.4 | 43.9 | 43.3 | 43.4 | 43.3 | 44.0 |
| C-9 | 61.2 | 52.7 | 50.9 | 52.8 | 52.6 | 52.9 | 52.8 | 61.2 | 52.9 | 61.3 | 61.3 | 52.8 | 52.5 |
| C-10 | 39.4 | 40.9 | 38.5 | 41.1 | 41.1 | 42.1 | 42.0 | 39.6 | 41.1 | 39.4 | 39.6 | 41.9 | 41.7 |
| C-11 | 198.7 | 199.8 | 199.6 | 199.6 | 199.4 | 199.6 | 199.5 | 198.8 | 199.5 | 198.7 | 198.7 | 199.8 | 200.6 |
| C-12 | 128.4 | 128.5 | 128.3 | 128.3 | 128.2 | 128.3 | 128.5 | 128.6 | 128.3 | 128.3 | 128.7 | 128.3 | 128.5 |
| C-13 | 169.3 | 169.4 | 169.5 | 169.7 | 169.2 | 169.6 | 169.3 | 169.2 | 169.4 | 169.6 | 169.1 | 170.0 | 170.7 |
| C-14 | 45.2 | 45.1 | 45.0 | 45.0 | 44.9 | 45.0 | 45.1 | 45.3 | 45.0 | 45.2 | 45.3 | 45.1 | 45.3 |
| C-15 | 26.2 | 26.4 | 26.3 | 26.3 | 26.3 | 26.4 | 26.4 | 26.3 | 26.4 | 26.2 | 26.4 | 26.4 | 26.4 |
| C-16 | 26.2 | 26.5 | 26.4 | 26.5 | 26.4 | 26.5 | 26.5 | 26.4 | 26.5 | 26.3 | 26.4 | 26.5 | 26.7 |
| C-17 | 31.7 | 31.4 | 31.6 | 31.7 | 31.6 | 31.8 | 32.0 | 31.8 | 31.7 | 31.4 | 31.7 | 31.8 | 31.8 |
| C-18 | 48.2 | 48.2 | 48.3 | 48.3 | 48.0 | 48.1 | 48.1 | 48.1 | 48.1 | 48.0 | 48.0 | 48.2 | 48.4 |
| C-19 | 41.0 | 40.9 | 43.6 | 43.7 | 43.5 | 41.1 | 44.5 | 41.0 | 43.6 | 41.7 | 41.8 | 41.1 | 44.6 |
| C-20 | 43.8 | 43.8 | 43.9 | 50.8 | 50.7 | 43.7 | 50.8 | 43.9 | 51.1 | 43.2 | 44.5 | 43.7 | 50.4 |
| C-21 | 30.9 | 30.8 | 31.1 | 31.0 | 31.0 | 31.4 | 31.6 | 31.1 | 31.2 | 31.8 | 32.2 | 31.4 | 31.6 |
| C-22 | 37.6 | 37.7 | 37.7 | 37.6 | 37.5 | 37.4 | 37.4 | 37.6 | 37.6 | 37.3 | 37.4 | 37.4 | 37.5 |
| C-23 | 31.7 | 114.2 | 114.2 | 114.1 | 114.1 | 114.2 | 114.2 | 32.2 | 114.3 | 31.8 | 32.2 | 114.3 | 114.2 |
| C-24 | 25.9 | 23.4 | 23.3 | 23.4 | 23.4 | 23.4 | 23.4 | 25.9 | 23.4 | 25.9 | 25.9 | 23.3 | 23.2 |
| C-25 | 17.4 | 19.5 | 19.4 | 19.5 | 19.4 | 19.5 | 19.5 | 17.4 | 19.4 | 17.4 | 17.4 | 19.5 | 19.4 |
| C-26 | 18.0 | 18.6 | 18.6 | 18.6 | 18.5 | 18.6 | 18.6 | 18.2 | 18.6 | 18.0 | 18.2 | 18.6 | 18.5 |
| C-27 | 23.0 | 23.8 | 23.4 | 23.1 | 23.2 | 23.2 | 23.3 | 23.1 | 23.3 | 23.0 | 23.1 | 23.2 | 23.1 |
| C-28 | 28.2 | 28.5 | 28.5 | 29.2 | 29.1 | 29.5 | 29.4 | 28.4 | 28.9 | 29.3 | 29.3 | 29.4 | 29.7 |
| C-29 | 28.1 | 28.4 | 28.2 | 28.2 | 28.1 | 29.2 | 29.2 | 28.2 | 28.3 | 28.5 | 28.4 | 29.1 | 29.1 |
| C-30 | 176.7 | 181.8 | 176.9 | 174.2 | 174.2 | 174.3* | 174.3* | 175.6 | 176.2 | 174.5 | 173.9 | 174.8 | 174.5 |
| OCH$_3$ | 51.6 | | 51.7 | 51.5 | 51.4 | 51.5 | 51.5 | | | | | | |
| OCH(CH$_3$)$_2$ | | 50.6 | | 67.3 | | | | | | | | | |
| OCH(CH$_3$)$_2$ | | 21.8, 21.8 | | 21.6, 21.8 | | | | | | | | | |
| OCH$_2$ | | | | | 66.1 | | | 66.2 | 66.2 | | | | |
| 1' | | | | | 136.0 | | 137.8 | 136.0 | 136.1 | | 137.8 | | 137.9 |
| 2' | | | | | 128.3 | | 120.1 | 128.2 | 128.2 | | 120.2 | | 121.4 |
| 3' | | | | | 128.5 | | 129.0 | 128.5 | 128.6 | | 128.7 | | 128.7 |
| 4' | | | | | 128.3 | | 124.4 | 128.3 | 128.4 | | 124.4 | | 124.4 |
| 5' | | | | | 128.5 | | 129.0 | 128.5 | 128.6 | | 128.7 | | 128.7 |
| 6' | | | | | 128.3 | | 120.1 | 128.2 | 128.2 | | 120.2 | | 121.4 |
| NH—CH(CH$_3$)$_2$ | | | | | | 50.8 | | | | 41.0 | | 50.8 | |
| NH—CH(CH$_3$)$_2$ | | | | | | 22.7 | | | | 22.6 | | 22.6 | |
| | | | | | | 22.9 | | | | 22.7 | | 22.9 | |

*Signals could be interchanged in the same column.

Example V

Biological Analysis for the Anti-Inflammatory and Anti-Oxidant Activities of the 18β-Glycyrrhetinic Acid Derivatives In the present invention, the anti-inflammatory activity of various compounds is determined by the inhibitory effect on the chemical mediators released by the neutrophil and macrophage.

Inhibition on the Superoxide Anion

Compound stock solution (30 mM in DMSO) is prepared and stored at −25° C. before experiment. In the superoxide anion generation experiments, neutrophils isolated from the peripheral blood of the rats are stimulated with formyl-Met-Leu-Phe (fMLP, 0.3 μM)/Cytochalasin B (CB, 5 μg/mL) for 30 min in the presence of cytochrome c, and the superoxide anion generation is measured in terms of superoxide dismutase-inhibitable cytochrome c reduction.

Figure 4:
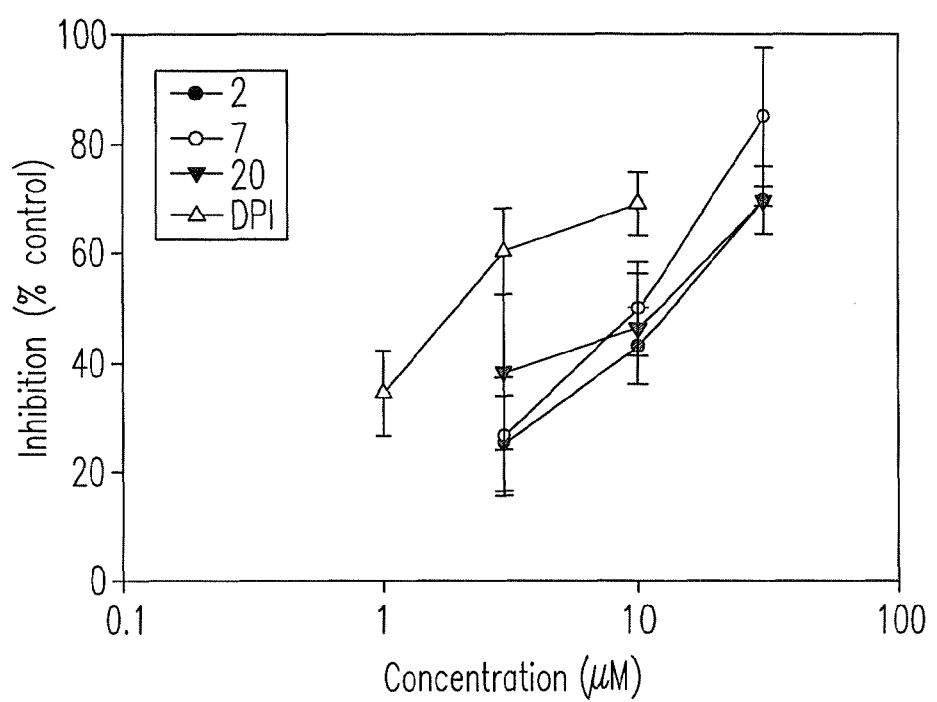
FIG. 4 is a diagram showing the inhibitory effect of DPI and the compounds 2, 7, and 20 on the superoxide anion formation in rat neutrophils stimulated by fMLP/CB, wherein the DPI is a positive control and the inhibitory effect of each compound is represented by percentage in comparison with the control group where data are presented as means±SD (n=3-6).

Please refer to FIG. 4, which is a diagram showing the inhibitory effect of DPI and the compounds 2, 7 and 20 on the superoxide anion formation in rat neutrophils stimulated by fMLP/CB. As shown in FIG. 4, all of the DPI and the compounds 2, 7 and 20 have concentration-dependent inhibitory effects with IC$_{50}$ values of 2.7±2.0, 10.3±5.2, 7.0±2.0, and 9.8±5.2 μM (as shown in Table 2 (A), wherein the IC$_{50}$ value represents the concentration of a compound inhibiting 50% superoxide anion generation).

Figure 5:
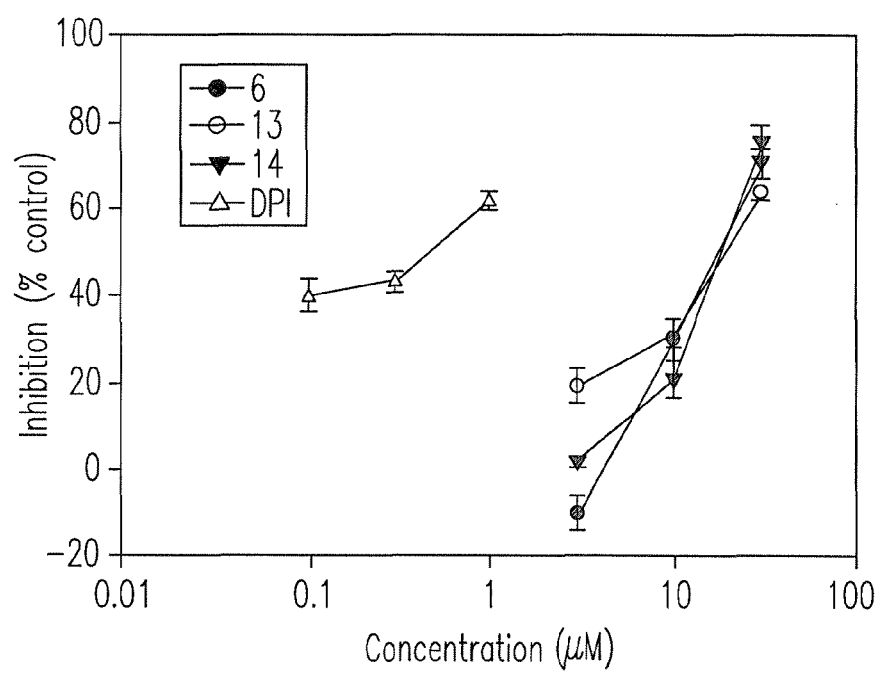
FIG. 5 is a diagram showing the inhibitory effect of DPI and the compounds 6, 13, and 14 on the superoxide anion formation in rat neutrophils stimulated by PMA, wherein the DPI is a positive control and the inhibitory effect of each compound is represented by percentage in comparison with the control group where data are presented as means±SD (n=3-6).

Please refer to FIG. 5, which is a diagram showing the inhibitory effect of DPI and the compounds 6, 13 and 14 on the superoxide anion formation in rat neutrophils stimulated by PMA. As shown in FIG. 5, all of the DPI and the compounds 6, 13 and 14 have concentration-dependent inhibitory effects with IC$_{50}$ values of 1.8±0.4, 12.9±1.8, 17.0±1.5, and 15.6±1.7 μM (as shown in Table 2 (A)). Other compounds synthesized by using the method of the present invention are less potent in inhibiting the generation of the superoxide anion while compared with the compounds in FIGS. 4 and 5, however, some compounds still have inhibitory activity.

TABLE 2

The inhibitory effect of 18β-GA derivatives on the superoxide anion formation from rat neutrophils stimulated with fMLP/CB or PMA (A), the accumulation of $NO_2^-$ in RAW 264.7 cells stimulated with LPS (B), and TNF-α formation from RAW 264.7 cells stimulated with LPS (C).

| Compound | $IC_{50}^a$ (μM) (A) fMLP/CB | PMA | $IC_{50}^a$ (μM) (B) RAW 264.7 | $IC_{50}^a$ (μM) (C) RAW 264.7 |
|---|---|---|---|---|
| 2 | 10.3 ± 5.2 | | >30 (45.6 ± 9.1) | |
| 3 | | | | 1.3 ± 0.4 |
| 5 | >3 (27.4 ± 9.2) | >3 (−8.2 ± 11.8) | >3 (3.0 ± 4.2) | >3 (−0.7 ± 2.7) |
| 6 | | 12.9 ± 1.8 | | |
| 7 | 7.0 ± 2.0 | | | |
| 8 | >10 (81.9 ± 7.4) | >10 (7.4 ± 3.1) | >10 (29.6 ± 10.0) | >10 (21.2 ± 8.7) |
| 9 | >1 (48.8 ± 6.6) | >1 (−7.0 ± 3.0) | >30 (39.8 ± 5.4) | >30 (38.4 ± 14.6) |
| 10 | | | | 26.1 ± 14.7 |
| 11 | | | >30 (44.3 ± 10.5) | |
| 12 | >30 (−2.5 ± 11.9) | >10 (28.7 ± 15.9) | >30 (43.0 ± 4.3) | >30 (47.0 ± 1.3) |
| 13 | | 17.0 ± 1.5 | >30 (44.5 ± 4.2) | 13.7 ± 4.3 |
| 14 | | 15.6 ± 1.7 | 13.1 ± 5.0 | |
| 15 | | | | 15.5 ± 3.2 |
| 16 | >30 (−22.9 ± 7.6) | >30 (−10.7 ± 10.2) | >10 (−2.3 ± 4.6) | >10 (25.3 ± 9.9) |
| 17 | | | | 2.3 ± 5.0 |
| 18 | >30 (2.7 ± 12.5) | >30 (48.2 ± 8.4) | >10 (30.0 ± 11.9) | >10 (9.7 ± 4.7) |
| 19 | >10 (−1.6 ± 4.4) | >3 (26.9 ± 3.0) | >30 (20.5 ± 2.7) | >30 (45.2 ± 14.6) |
| 20 | 9.8 ± 5.2 | | | |
| 21 | | | | 27.7 ± 7.2 |
| DPI | 2.7 ± 2.0 | 1.8 ± 0.4 | | |
| 1400 W | | | 1.5 ± 0.2 | |
| Genistein | | | | 26.5 ± 9.1 |

$^a$When 50% inhibition could not be reached at the highest concentration, the % of inhibition is given in parentheses.

These results indicate that introduction of a lipophilic alkyl group at C-30 of 18β-GA derivatives might attenuate their inhibitory effects on fMLP/CB-induced responses while introduction of a lipophilic group at C-30 of compound 5 or a benzylester moiety at C-30 such as compound 13 or an isopropylcarbamoyl group at C-30 such as compound 14 significantly enhance the inhibitory effects on PMA-induced responses. As shown in FIG. 1 also reveals that cleavage of ring A of compound 2 to afford compounds with 3,4-seco-structure, such as compound 7, enhances its inhibitory effect on fMLP/CB-induced responses. Introduction of a lipophilic moiety at C-30 or C-3 of compounds 14, 15, or 21 weakened the inhibitory activity on fMLP/CB-induced response, but introduction of an isopropylcarbamoyl moiety at C-30 of such as compound 20 enhances the inhibitory activity on response induced by same inducer (FIG. 1). As shown in FIG. 2, lactone derivative from 18β-GA such as compound 6 displays stronger inhibitory effect being preferably concentration-dependent on PMA-induced response than those of compounds 13 and 14. The result indicates that cleavage of ring A of compound 6 and introduction of a side chain larger than the methyl group at C-30 attenuate the inhibitory effect on PMA-induced response. Because fMLP and PMA activate NADPH oxidase to produce superoxide anion through different cellular signaling mechanism, these 18β-GA derivatives indicated different inhibitory effects on fMLP/CB- and PMA-induced responses.

Inhibition on the Nitric Oxide and the Tumor Necrosis Factor (TNF-α)

Murine macrophage-like cell line RAW 264.7 cells are plated in 96-well plate, and incubated with test compounds for 1 h at 37° C. before stimulation with 1 lg/mL of lipopolysaccharide (LPS) for 24 h. Nitric oxide (NO) in the cell medium is determined by the Griess reaction. In Western blot analysis, cells are washed with PBS twice and harvested in Laemmli sodium dodecyl sulfate (SDS) sample buffer to lyse the cells. Cell lysates are separated by 10% SDS-PAGE, and electrophoretically transferred to the poly(vinylidene difluoride) membranes. Membranes are blocked for 1 h at room temperature in TBST buffer (10 mM Tris-HCl, pH 8.0, 150 mM NaCl and 0.1% Tween 20) containing 5% nonfat milk. Membranes are washed with TBST buffer and then incubated with a monoclonal anti-iNOS antibody (1:1000 dilution) for 1 h. Following washed with TBST buffer, horseradish peroxidase-labeled anti-mouse IgG (1:10,000 dilution) is added therein at room temperature for 1 h. The blots are developed using ECL Western blotting reagents. Secretory levels of TNF-α in culture supernatants are determined by the EIA kit according to the procedure of manufacturer.

Figure 6:
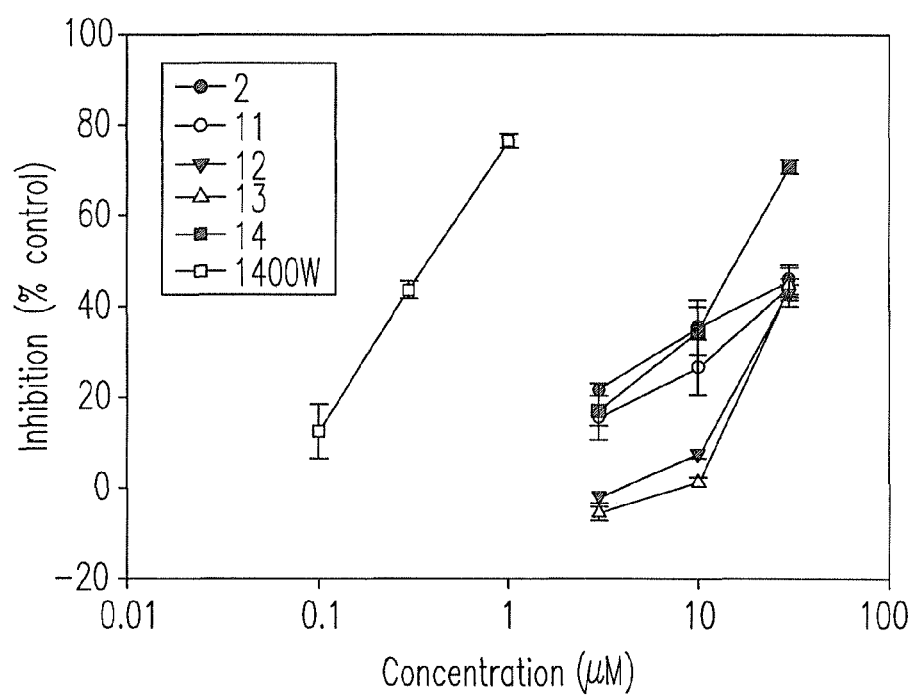
FIG. 6 is a diagram showing the inhibitory effect of 1400 W and the compounds 2, 11, 12, 13, and 14 on the nitrite formation in RAW 264.7 cells stimulated by LPS, wherein the 1400 W is a positive control and the inhibitory effect of each compound is represented by percentage in compare with the control group where data are presented as means±SD (n=3-6).

Please refer to FIG. 6, which is a diagram showing the inhibitory effect of 1400 W and the compounds 2, 11, 12, 13 and 14 on the nitrite formation in RAW 264.7 cells stimulated by LPS. Nitrite is a stable metabolite of NO in the media based on Griess reaction. As shown in FIG. 6, LPS-induced NO production and this effect is concentration dependently suppressed by the LPS inhibitor (N-(3-aminomethyl)benzylacetamidine, 1400 W) and compound 14 with $IC_{50}$ values of 1.5±0.2 and 13.1±5.0 μM (Table 2), respectively while compounds 2, 11, 12, and 13 each at 30 μM indicated about 40% of inhibitory effect on NO accumulation in the media induced by LPS. The above observation shows that a lipophilic group substituted at C-3 or C-30 of 3,4-seco-type derivatives from 18β-GA might enhance the suppression of NO accumulations in the media induced by LPS. To determine whether the inhibition of NO production in RAW 264.7 cells is attributed to the decrease of iNOS protein expression, Western blotting analysis is performed. Unstimulated cells expressed very low level of iNOS protein, whereas LPS 50 ng/mL induced a large amount of iNOS protein expression. Compound 14 significantly inhibited the iNOS protein expression. Thus, the blockade of iNOS transcription has a critical role as evidenced from the parallelism of the inhibition of NO production and iNOS protein expression by compound 14.

Figure 7:
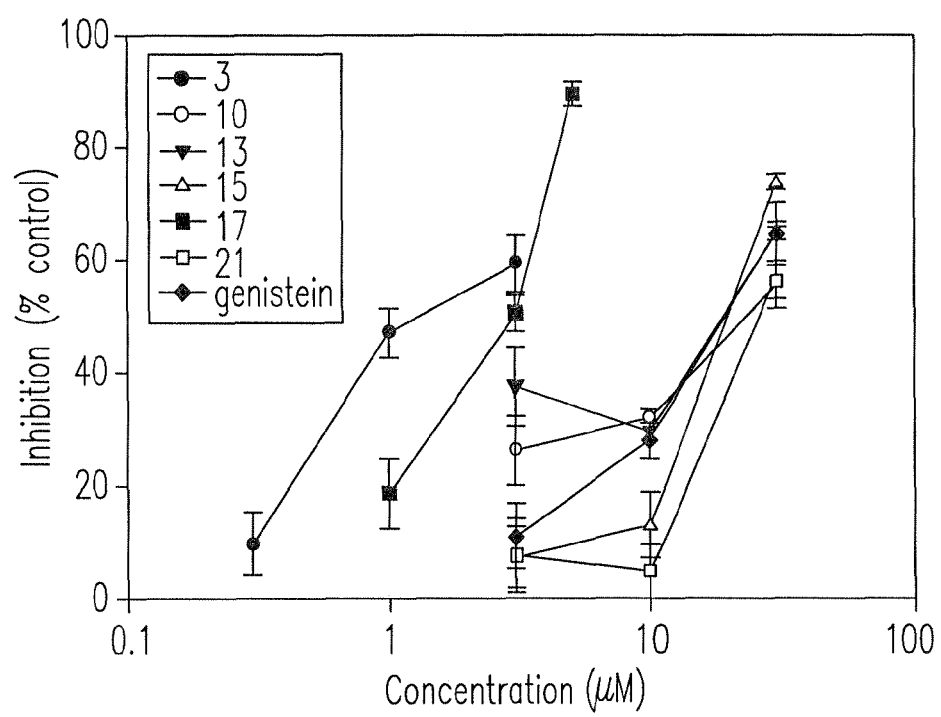
FIG. 7 is a diagram showing the inhibitory effect of genistein and the compounds 3, 10, 13, 15, 17, and 21 on the TNF-α formation in RAW 264.7 cells stimulated by LPS, wherein the genistein is a positive control and the inhibitory effect of each compound is represented by percentage in comparison with the control group where data are presented as means±SD (n=3-6).

Please further direct to FIG. 7, which is a diagram showing the inhibitory effect of genistein and the compounds 3, 10, 13, 15, 17 and 21 on the TNF-α formation in RAW 264.7 cells stimulated by LPS. As shown in FIG. 7 and Table 2, genistein, compounds 3, 10, 13, 15, 17, and 21 strongly and concentration dependently inhibited TNF-α generation in LPS-stimulated RAW 264.7 cells with $IC_{50}$ values of 26.5±9.1, 1.3±0.4, 26.1±14.7, 13.7±4.3, 15.5±3.2, 2.3±0.5, 27.7±7.2 μM, respectively. Among these compounds, the suppression effect of TNF-α generation in RAW 264.7 cells stimulated with LPS by these compounds except for compound 21 are stronger than that of positive control. It is suggested that the esterification of C-30 at 18β-GA enhances the suppressed effect on TNF-α generation while reduction of C-3-OH of 18β-GA or cleavage of ring A attenuates the inhibition of TNF-α generation on LPS-stimulated response. The esterification of C-30 at 3,4-seco-type derivatives from 18β-GA with benzyl alcohol strongly enhances the inhibitory effect on TNF-α generation while amidation with isopropylamine attenuate the inhibition of TNF-α generation on LPS-stimulated response.

Example VI

Assay of Inhibition of Oxidative DNA Damage

A mixture of the plasmid pBR322 DNA (1 μg/lL) and xanthine (2 mM)/xanthine oxidase (0.7 U/mL) in 10 mM phosphate buffer (pH 7.4) is incubated for 20 min with 500 μlM of superoxide dismutase, quercetin, or compounds 2, 6, 7, 13, 14, and 20 in a total volume of 20 μL at 37° C., respectively. After incubating for 20 min, a 15 μL aliquot of mixture is loaded into 1.0% agarose gel containing ethidium bromide (0.05 μg/mL) in Tris-acetate-ethylenediaminetetraacetic acid (EDTA) buffer. The electrophoresis is carried out for 30 min at 100V. Then the gels are illuminated with UV light and photographed.

ROS have been known to damage many biological macromolecules, for instance, with DNA being a significant target. The ability of 18β-GA derivatives to inhibit the DNA damage caused by $O_2^-$. (generated by xanthine (XA)/XO) is studied in vitro by agarose gel electrophoresis. Compounds 2, 6, 7, 13, 14, and 20 revealed significant inhibitory effects on superoxide anion formation released from rat neutrophils activated by fMLP/CB or PMA and showed significant protective effects on oxidative DNA damage caused by $O_2^-$. The above results clearly revealed that these compounds may have inhibitory effect on XO or scavenging effect on the free radical. For determined the antioxidant activities of these compounds, the radical scavenging activities and XO inhibitory activities of these compounds are analyzed.

Example VII

Assay of Xanthine Oxidase Activity

The xanthine oxidase activity with xanthine as the substrate is measured at 25° C., according to the protocol of Kong and associates (*Cell Mol. Life Sci.* 57, 500-505) with modification. The assay mixture consisting of 50 μL of test solution, 60 μL of 70 mM phosphate buffer (pH 7.5), and 30 μL of enzyme solution (0.1 U/mL in 70 mM phosphate buffer (pH 7.5)) is prepared immediately before use. After preincubation at 25° C. for 15 min, the reaction is initiated by addition of 60 μL of substrate solution (150 μM xanthine in the same buffer).

The reaction is monitored at 295 nm. The xanthine oxidase activity is expressed as micromoles of uric acid per minute.

Figure 8:
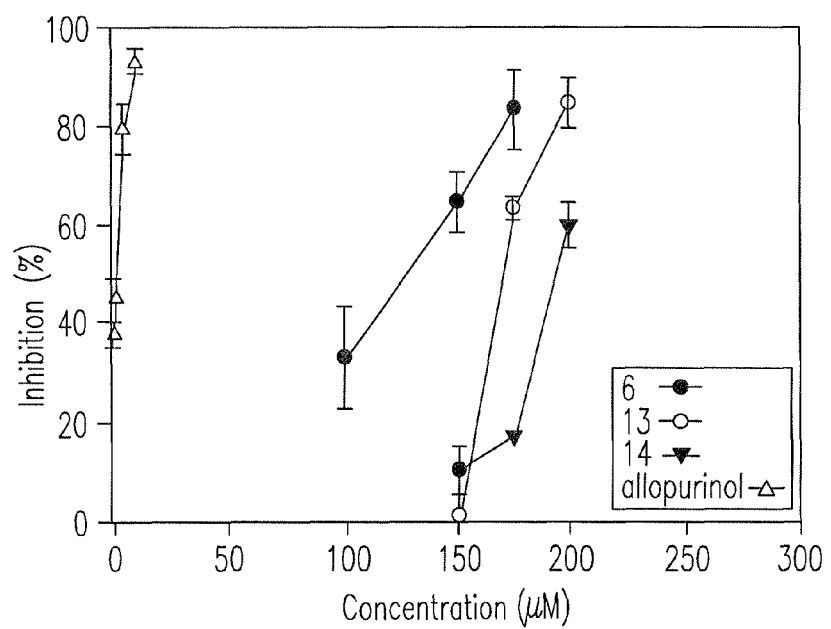
FIG. 8 is a diagram showing the inhibitory effect on XO of the compounds 6, 13, 14 and allopurinol, wherein the allopurinol is a positive control and the inhibitory effect of each compound is represented by percentage in comparison with the control group where data are presented as means±SD (n=3-6).

Please refer to FIG. 8, which is a diagram showing the inhibitory effect on XO of the compounds 6, 13, 14 and allopurinol. As shown in FIG. 8, the genistein, the compounds 6, 13, 14, 22, and allopurinol significantly inhibit the XO activity in a concentration-dependent manner with $IC_{50}$ values of 131.5±2.7, 175.0±0.9, 192.4±2.7, 186.1±1.0, and 2.0±0.7 μM, respectively. Compounds 2, 7, and 20 weakly inhibit the XO activity. The compounds 6, 13 and 14 having inhibitory effects on XO activity also show inhibitory effect on the formation of superoxide anion in PMA-stimulated rat neutrophills. This result showed that the suppression of superoxide anion formation by these compounds in rat neutrophils stimulated with PMA may correlate with XA/XO system while the suppression of superoxide anion formation by compounds 2, 7, and 20 in rat neutrophils stimulated with fMLP/CB did not correlate with XA/XO system. The above results also indicated that the cleavage of lactone ring of the compound 6 attenuates the inhibitory effect on XO activity.

In summary, the 18β-GA derivatives synthesized by the method in the present invention are proved as having the anti-oxidant and anti-inflammatory effect, which are valuable in clinical for treating or preventing the central or peripheral inflammatory diseases related to the increase of the nitric oxide formation. In another aspect, the inhibition of the TNF-α formation of the 18β-GA derivatives in the present invention in rat neutrophils is also valuable in treating or preventing some inflammatory diseases related to the TNF-α formation and septic shock.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A method for synthesizing a chemical compound having a structure of

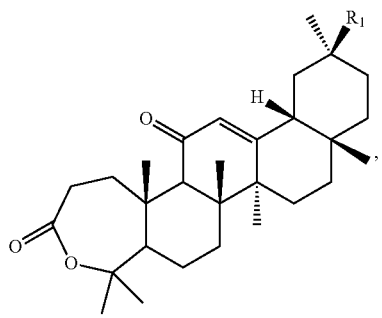

wherein $R_1$ is one of $CONHCH(CH_3)_2$ and $CONHC_6H_5$, the method comprising steps of:

(a) oxidizing 18β-glycyrrhetinic acid using $CrO_3$ in dimethyl formamide to form a first compound having a structure of

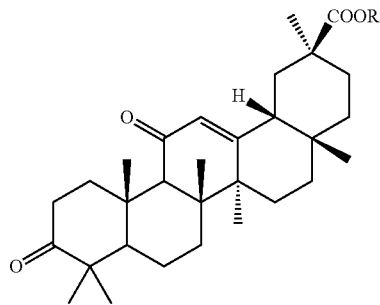

where R is H;
(b) oxidizing the first compound with m-chloroperbenzoic acid to form a lactone compound having a structure of

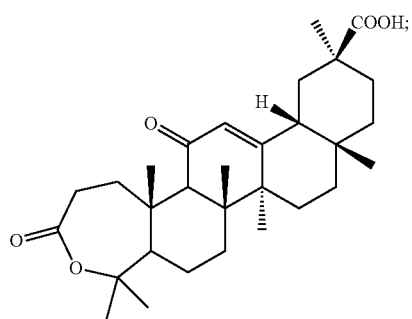

and
(c) amidating an acid group at C-30 of the lactone compound with an amine to obtain the chemical compound, wherein the amine is an isopropylamine when $R_1$ is CONHCH($CH_3$)$_2$, and the amine is an aniline when $R_1$ is CONHC$_6$H$_5$.

2. A method for synthesizing a chemical compound having a first structure of

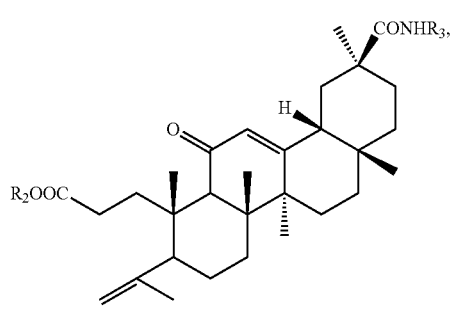

where $R_2$ is H, and $R_3$ is one of CH(CH$_3$)$_2$ and C$_6$H$_5$, the method comprising a step of cleaving a lactone ring of an 18β-glycyrrhetinic acid derivative having a second structure of

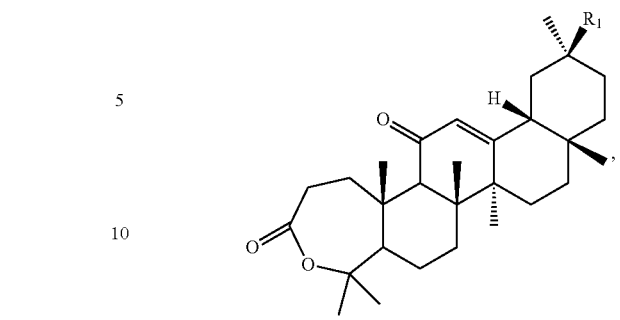

in the presence of ρ-toluenesulfonic acid in methylene chloride to obtain the chemical compound, wherein $R_3$ of the first structure is CH(CH$_3$)$_2$ when $R_1$ of the second structure is CONHCH(CH$_3$)$_2$, and $R_3$ of the first structure is C$_6$H$_5$ when $R_1$ of the second structure is CONHC$_6$H$_5$.

3. A method for synthesizing a chemical compound having a first structure of

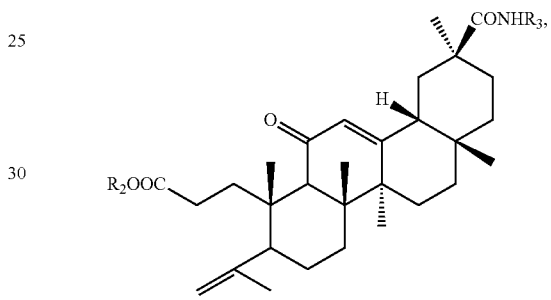

where $R_2$ is CH$_3$, and $R_3$ is one of CH(CH$_3$)$_2$ and C$_6$H$_5$, the method comprising a step of treating an 18β-glycyrrhetinic acid derivative having a second structure of

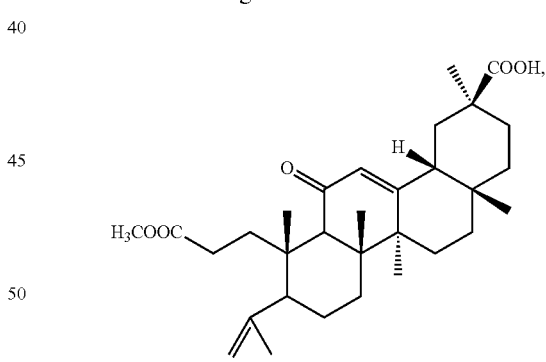

with an amine to obtain the chemical compound, wherein the amine is isopropylamine when $R_3$ is CH(CH$_3$)$_2$, and the amine is aniline when $R_3$ is C$_6$H$_5$.

* * * * *